US011534508B2

(12) United States Patent
Ito et al.

(10) Patent No.: US 11,534,508 B2
(45) Date of Patent: Dec. 27, 2022

(54) METHOD FOR PRODUCING STERILIZED OXYGEN-ABSORBING MULTILAYER BODY

(71) Applicant: MITSUBISHI GAS CHEMICAL COMPANY, INC., Tokyo (JP)

(72) Inventors: Fumihiro Ito, Tokyo (JP); Satoshi Okada, Kanagawa (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 813 days.

(21) Appl. No.: 16/483,972

(22) PCT Filed: Feb. 6, 2018

(86) PCT No.: PCT/JP2018/003981
§ 371 (c)(1),
(2) Date: Aug. 6, 2019

(87) PCT Pub. No.: WO2018/147262
PCT Pub. Date: Aug. 16, 2018

(65) Prior Publication Data
US 2020/0009278 A1  Jan. 9, 2020

(30) Foreign Application Priority Data
Feb. 8, 2017 (JP) .............................. JP2017-021416

(51) Int. Cl.
B32B 1/02 (2006.01)
A61L 2/08 (2006.01)
B32B 27/08 (2006.01)
B32B 27/32 (2006.01)
B32B 27/36 (2006.01)
B65D 65/40 (2006.01)
B65D 81/26 (2006.01)
C08G 63/199 (2006.01)
C08G 63/88 (2006.01)
B65B 55/06 (2006.01)
B65B 55/02 (2006.01)
B65B 55/08 (2006.01)
B65B 55/04 (2006.01)
B32B 38/00 (2006.01)

(52) U.S. Cl.
CPC ................. A61L 2/08 (2013.01);
B32B 1/02 (2013.01); B32B 27/08 (2013.01);
B32B 27/325 (2013.01); B32B 27/36 (2013.01); B32B 38/0008 (2013.01); B32B 38/0036 (2013.01); B65B 55/02 (2013.01); B65B 55/04 (2013.01); B65B 55/06 (2013.01); B65B 55/08 (2013.01); B65D 65/40 (2013.01); B65D 81/266 (2013.01); C08G 63/199 (2013.01); C08G 63/88 (2013.01); A61L 2202/11 (2013.01); B32B 2307/724 (2013.01); B32B 2310/08 (2013.01); B32B 2310/085 (2013.01); B32B 2310/0806 (2013.01); B32B 2310/0856 (2013.01); B32B 2310/0887 (2013.01); B32B 2439/00 (2013.01)

(58) Field of Classification Search
CPC ......... C08G 63/88; B65B 55/02; B65B 55/04; B65B 55/06; B32B 27/34; B32B 27/36
USPC .......................................................... 422/22
See application file for complete search history.

(56) References Cited

U.S. PATENT DOCUMENTS

| 10,035,129 | B2 | 7/2018 | Okada et al. | |
|---|---|---|---|---|
| 2009/0135345 | A1 | 5/2009 | Yajima et al. | |
| 2011/0260358 | A1 | 10/2011 | Wang et al. | |
| 2012/0045362 | A1 | 2/2012 | Kleiner et al. | |
| 2014/0110885 | A1 | 4/2014 | Wang et al. | |
| 2014/0234164 | A1 | 8/2014 | Kleiner et al. | |
| 2014/0308405 | A1* | 10/2014 | Okada ............. | C08G 63/64 428/35.8 |
| 2014/0373485 | A1* | 12/2014 | Okada ............. | B65D 81/26 604/199 |
| 2015/0298887 | A1* | 10/2015 | Okada ............. | B32B 27/36 428/36.6 |
| 2015/0368022 | A1* | 12/2015 | Okada ............. | B32B 27/32 428/354 |
| 2016/0017092 | A1* | 1/2016 | Iwamoto ......... | C08G 63/181 206/524.4 |
| 2016/0031628 | A1 | 2/2016 | Ito et al. | |

(Continued)

FOREIGN PATENT DOCUMENTS

| JP | 2000-5283 | 1/2000 |
|---|---|---|
| JP | 3785473 B2 | 3/2006 |
| JP | 2007-99366 | 4/2007 |

(Continued)

OTHER PUBLICATIONS

Official Communication issued in International Bureau of WIPO Patent Application No. PCT/JP2018/003981, dated Apr. 24, 2018.

Primary Examiner — Terressa Boykin
(74) Attorney, Agent, or Firm — Greenblum & Bernstein, P.L.C.

(57) ABSTRACT

A method for producing a sterilized oxygen-absorbing multilayer body is provided. The method may include:
irradiating with radiation an oxygen-absorbing multilayer body comprising at least an oxygen-absorbing layer containing a transition metal catalyst and a thermoplastic resin (a) having a tetralin ring as a structural unit and a layer containing a thermoplastic resin (b); and
heating the oxygen-absorbing multilayer body which has been irradiated with radiation in the sterilizing step at a temperature of the glass transition temperature of the thermoplastic resin (a) minus 20° C. or more and lower than the glass transition temperature of the thermoplastic resin (a) for 50 hours or more.

13 Claims, No Drawings

(56) References Cited

U.S. PATENT DOCUMENTS

2017/0009035 A1* 1/2017 Ito ............................ B32B 27/06
2017/0137203 A1* 5/2017 Arakawa ................... B32B 7/12

FOREIGN PATENT DOCUMENTS

| JP | 2013-540462 | 11/2013 |
| JP | 2015-217971 | 12/2015 |
| JP | 2016-174731 | 10/2016 |
| JP | 2018-16723 | 2/2018 |
| KR | 2015-0126393 A | 11/2015 |
| KR | 2015-0128652 A | 11/2015 |
| TW | 201536195 A | 10/2015 |
| WO | 2013/077436 | 5/2013 |
| WO | 2013/089268 | 6/2013 |
| WO | 2013/118882 | 8/2013 |
| WO | 2015/119230 | 8/2015 |

* cited by examiner

METHOD FOR PRODUCING STERILIZED OXYGEN-ABSORBING MULTILAYER BODY

TECHNICAL FIELD

The present invention relates to a method for producing a sterilized oxygen-absorbing multilayer body.

BACKGROUND ART

Gamma sterilization using $Co^{60}$, which is a radioisotope of Co, as a radiation source has been common for many years as a radiation sterilization method of containers used for food, beverages, drugs, cosmetics, and the like. The radiation sterilization method further includes treatment by X-rays or electron beams in addition to gamma sterilization. The radiation sterilization has been widely spreading as a sterilization treatment method because containers can be treated at a low temperature, in a short time, and at a relatively low cost.

On the other hand, for the purpose of preventing oxidation by oxygen of various articles liable to change in quality or deteriorate in response to the influence of oxygen, which are typified by food, beverages, drugs, and cosmetics, to thereby store them for a long period of time, there has been used an oxygen absorber to remove oxygen in a package in which these articles are received.

Further, there have been developed oxygen-absorbing resin compositions each containing a transition metal catalyst and a polymer having a predetermined tetralin ring and multilayer containers using the same (refer to Patent Literatures 1 to 3 below).

Furthermore, a technique of suppressing coloration even after performing sterilization by irradiation with radiation has been proposed (see Patent Literature 4 below).

CITATION LIST

Patent Literature

Patent Literature 1: International Publication No. WO 2013/077436
Patent Literature 2: International Publication No. WO 2013/089268
Patent Literature 3: International Publication No. WO 2013/118882
Patent Literature 4: International Publication No. WO 2015/119230

SUMMARY OF INVENTION

Technical Problem

In the technique of Patent Literature 4 (International Publication No. WO2015/119230), coloration caused by irradiation with radiation can be faded even after sterilization by irradiation with radiation by a heat treatment. However, in the case of using materials such as a multilayer container, treatment at high temperature should be avoided so as to prevent deformation of the container depending on the resins combined or purposes of use. Furthermore, some resin may be colored by heating.

Moreover, sterilization generates radical products, which in turn may cause odor. In a film without oxygen-absorbing power, such odor can be reduced by, for example, leaving the film after sterilization for a few weeks. However, for materials with oxygen-absorbing power, leaving them for a long time in the presence of oxygen is not preferred for properties of the product.

To solve the above problems, the An object of the present invention is to provide a method for producing a sterilized oxygen-absorbing multilayer body which can reduce generation of odor and prevent deformation of containers and coloration due to thermal degradation while keeping oxygen-absorbing power.

Solution to Problem

As a result of investigation of oxygen-absorbing multilayer bodies, the present inventors have found that the above problems can be solved by performing heat treatment under a specific condition after the sterilization treatment with radiation such as gamma rays, X-rays, and electron beams, even at low temperature where deformation of containers can be suppressed, and have completed the present invention.

Specifically, the present invention is as follows.

<1> A method for producing a sterilized oxygen-absorbing multilayer body, comprising:

a sterilizing step of irradiating with radiation an oxygen-absorbing multilayer body comprising at least an oxygen-absorbing layer containing a transition metal catalyst and a thermoplastic resin (a) having a tetralin ring as a structural unit and a layer containing a thermoplastic resin (b); and a heating step of heating the oxygen-absorbing multilayer body which has been irradiated with radiation in the sterilizing step at a temperature of the glass transition temperature of the thermoplastic resin (a) minus 20° C. or more and lower than the glass transition temperature of the thermoplastic resin (a) for 50 hours or more.

<2> The method for producing a sterilized oxygen-absorbing multilayer body according to <1>, wherein the oxygen-absorbing multilayer body comprises at least two layers containing a thermoplastic resin (b) and the oxygen-absorbing layer is disposed between the two layers containing a thermoplastic resin (b).

<3> The method for producing a sterilized oxygen-absorbing multilayer body according to <1> or <2>, wherein the glass transition temperature of the thermoplastic resin (a) ($Tg^1$) and the glass transition temperature of the thermoplastic resin (b) ($Tg^2$) have the relation represented by the following equation (A):

$$Tg^1 \le Tg^2 \le [Tg^1 + 10° C.] \qquad \text{Equation (A):}$$

<4> The method for producing a sterilized oxygen-absorbing multilayer body according to any one of <1> to <3>, wherein the heating time in the heating step is 50 hours or more and 120 hours or less.

<5> The method for producing a sterilized oxygen-absorbing multilayer body according to any one of <1> to <4>, wherein the heating temperature in the heating step is a temperature of the glass transition temperature of the thermoplastic resin (a) minus 20° C. or more and the glass transition temperature of the thermoplastic resin (a) minus 5° C. or less.

<6> The method for producing a sterilized oxygen-absorbing multilayer body according to any one of <1> to <5>, wherein the oxygen-absorbing multilayer body is heated in the presence of oxygen in the heating step.

<7> The method for producing a sterilized oxygen-absorbing multilayer body according to any one of <1> to <6>, wherein the thermoplastic resin (b) has a glass transition temperature of 60 to 80° C.

<8> The method for producing a sterilized oxygen-absorbing multilayer body according to any one of <1> to <7>, wherein the oxygen-absorbing multilayer body is an oxygen-absorbing multilayer container.

<9> The method for producing a sterilized oxygen-absorbing multilayer body according to any one of <1> to <8>, wherein
the thermoplastic resin (a) is a polyester compound comprising at least one structural unit having a tetralin ring selected from the group consisting of the following general formulas (1) to (4):

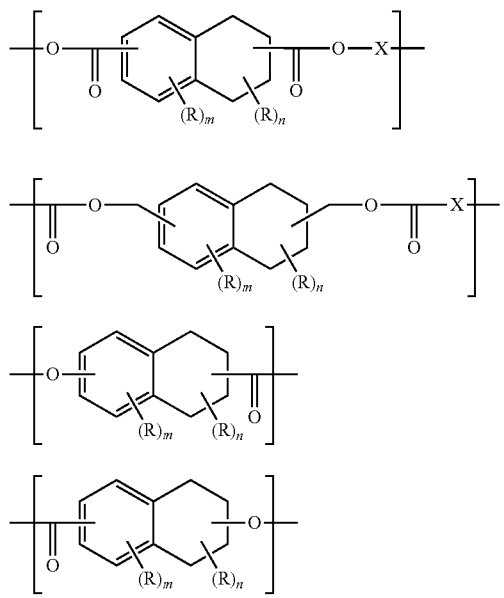

wherein R independently represents a hydrogen atom or a monovalent substituent; the monovalent substituent is at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, wherein the monovalent substituent may further have a substituent; m represents an integer of 0 to 3; n represents an integer of 0 to 7; at least one hydrogen atom is bonded to the benzylic position of the tetralin ring; and X represents a divalent group comprising at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

<10> The method for producing a sterilized oxygen-absorbing multilayer body according to any one of <1> to <9>, wherein the transition metal catalyst contains at least one transition metal selected from the group consisting of manganese, iron, cobalt, nickel, and copper.

<11> The method for producing a sterilized oxygen-absorbing multilayer body according to any one of <1> to <10>, wherein the transition metal catalyst is contained in an amount of 0.0001 to 10 parts by mass in terms of the amount of a transition metal based on 100 parts by mass of the thermoplastic resin (a).

<12> The method for producing a sterilized oxygen-absorbing multilayer body according to any one of <1> to <11>, wherein the thermoplastic resin (a) is a polyester compound comprising at least one structural unit having a tetralin ring selected from the group consisting of the following general formulas (5) to (7):

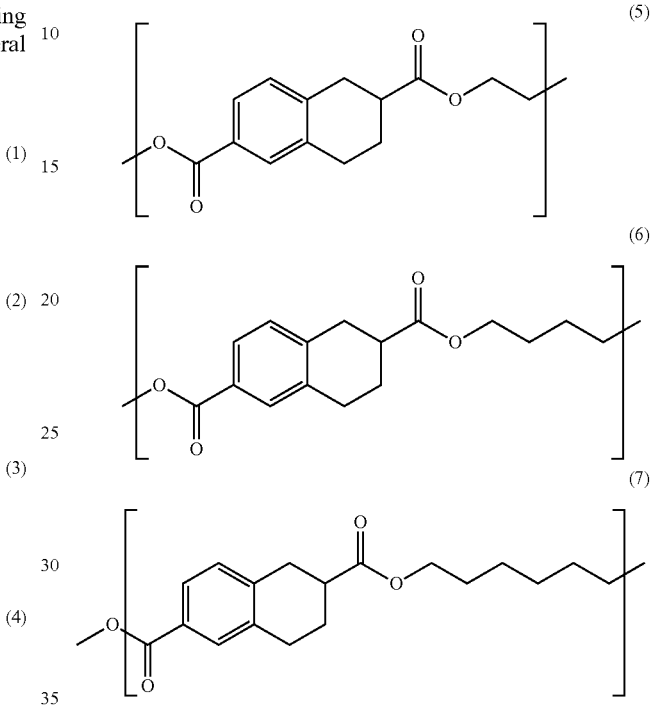

<13> The method for producing a sterilized oxygen-absorbing multilayer body according to any one of <1> to <12>, wherein the radiation is gamma rays, X-rays, or electron beams.

Advantageous Effects of Invention

The present invention can provide a method for producing a sterilized oxygen-absorbing multilayer body which can reduce generation of odor and prevent thermal deformation and coloration due to thermal degradation while keeping oxygen-absorbing power.

DESCRIPTION OF EMBODIMENTS

Hereinafter, the embodiment of the present invention (hereinafter simply referred to as "the present embodiment") will be described in detail. The present embodiment to be described below is for illustration purposes to describe the present invention and not intended to limit the present invention to the following contents. The present invention can be implemented by suitably modifying the contents within the scope of the present invention.

The method for producing a sterilized oxygen-absorbing multilayer body of the present embodiment (hereinafter sometimes referred to as "the production method of the present embodiment") comprises: a sterilizing step of irradiating with radiation an oxygen-absorbing multilayer body comprising at least an oxygen-absorbing layer containing a transition metal catalyst and a thermoplastic resin (a) having a tetralin ring as a structural unit (hereinafter sometimes simply referred to as "layer A") and a layer containing a thermoplastic resin (b) (hereinafter sometimes simply referred to as "layer B"); and a heating step of heating the oxygen-absorbing multilayer body which has been irradiated with radiation in the sterilizing step at a temperature of the glass transition temperature of the thermoplastic resin (a) minus 20° C. or more and lower than the glass transition temperature of the thermoplastic resin (a) for 50 hours or more.

When sterilization by irradiation with radiation is performed to produce a sterilized oxygen-absorbing multilayer body such as a multilayer container, carrying out heating at fairly high temperature (e.g., a temperature higher than the glass transition temperature of the thermoplastic resin (a) used for layer A) is advantageous to reduce, or fade, coloration caused by sterilization. However, when producing a sterilized oxygen-absorbing multilayer body such as a multilayer container, it is desired in some cases that the difference in the glass transition temperature between resins used for the respective layers should be reduced so as to improve, for example, moldability. If, for example, the difference in the glass transition temperature between the above layer A and layer B is reduced, it may be difficult to perform heat treatment at a temperature higher than the glass transition temperature of the thermoplastic resin (a) in the heating step after the sterilization of the container because of coloration due to thermal degradation or thermal deformation. Since odor generated in sterilization is thought to be caused by radical (ozone) produced by irradiation with radiation, such odor may also be reduced by leaving the material for a long time, for example, a few weeks or more, in the presence of oxygen (in air atmosphere). However, it is preferable for materials with oxygen-absorbing power that leaving them for a long time in the presence of oxygen should be avoided from the point of view of maintaining the oxygen-absorbing power.

According to the production method of the present embodiment, generation of odor can be effectively reduced and deformation of containers and coloration due to thermal degradation can be prevented while keeping oxygen-absorbing power by heating at a temperature of the glass transition temperature of the thermoplastic resin (a) minus 20° C. or more and lower than the glass transition temperature of the thermoplastic resin (a) for 50 hours or more, even when using, for example, a material in which the difference in the glass transition temperature between the layer A and the layer B is small as described above, although the action of the present embodiment is not limited to these. The respective components, steps and other matters will be described below.

[Oxygen-Absorbing Resin Multilayer Body]

In the present embodiment, an oxygen-absorbing multilayer body comprising at least an oxygen-absorbing layer containing a transition metal catalyst and a thermoplastic resin (a) having a tetralin ring as a structural unit (layer A) and a layer containing a thermoplastic resin (b) (layer B) is used.

The oxygen-absorbing multilayer body comprises at least two layers of an oxygen-absorbing layer (layer A) and a layer containing a thermoplastic resin (b) (layer B) (A/B structure).

The layer structure of the oxygen-absorbing multilayer body is not particularly limited. The number and types of layers A and layers B are not particularly limited. For example, the oxygen-absorbing multilayer body may have at least two layers containing the thermoplastic resin (b) (layer B), and the oxygen-absorbing layer (layer A) may be disposed between the two layers containing the thermoplastic resin (b) (layer B) (B/A/B structure). More specifically, the oxygen-absorbing multilayer body may have an A/B structure consisting of a layer A and a layer B as described above, or a three layer structure of B/A/B structure consisting of a layer A and two layers B. The structure may also be a five layer structure of B1/B2/A/B2/B1 consisting of a layer A and four layers B including two types: layer B1 and layer B2. The multilayer body of the present embodiment may have an optional layer such as an adhesive layer (layer AD) as necessary. The structure may be, for example, a seven layer structure of B1/AD/B2/A/B2/AD/B1. For the layer structure of the oxygen-absorbing multilayer body, those having at least three layers of a B/A/B structure are preferred.

Furthermore, in the oxygen-absorbing multilayer body, from the point of view of improving the moldability, the glass transition temperature of the thermoplastic resin (a) ($Tg^1$) and the glass transition temperature of the thermoplastic resin (b) ($Tg^2$) preferably have the relation represented by the following equation (A):

$$Tg^1 \leq Tg^2 \leq [Tg^1 + 10°\text{ C.}]$$ Equation (A):

The relation between the respective glass transition temperatures represented by the equation (A) is more preferably one represented by the following equation (A'), although the relation is not particularly limited.

$$Tg^1 \leq Tg^2 \leq [Tg^1 + 5°\text{ C.}]$$ Equation (A'):

Here, the "glass transition temperature of the thermoplastic resin (a)" and the "glass transition temperature of the thermoplastic resin (b)" may be measured by the method according to JIS K7121: 2012.

For example, when the oxygen-absorbing multilayer body has the above B/A/B structure, the glass transition temperature of the layer B ($Tg^2$) located on the inner layer and that on the outer layer may not be necessarily the same (in other words, the same material needs not be used for the respective layers B). It is preferable that the glass transition temperature of the respective B layers ($Tg^2$) and the glass transition temperature of the thermoplastic resin (a) ($Tg^1$) at least satisfy the relation of the equation (A). It is preferable that in the B/A/B structure, the material used for the respective layers B be the same in consideration of steps including multilayer extrusion.

[Oxygen-Absorbing Layer (Layer A)]

The method for producing the oxygen-absorbing layer (layer A) is not particularly limited as long as the oxygen-absorbing layer contains a transition metal catalyst and a thermoplastic resin (a) having a tetralin ring as a structural unit. The oxygen-absorbing layer may be formed by using, for example, an oxygen-absorbing resin composition containing a transition metal catalyst and a thermoplastic resin (a) having a tetralin ring as a structural unit. The oxygen-absorbing resin composition of the present embodiment is not limited at all as long as it contains a transition metal catalyst and a thermoplastic resin (a) having a tetralin ring as a structural unit, but a known material can be used for it. For example, as a thermoplastic resin (a), polymers each having a tetralin ring such as those described in International Publication No. WO 2013/077436, International Publication No. WO 2013/089268, and International Publication No. WO 2013/118882 can also be used.

(Thermoplastic Resin (a))

From the point of view of oxygen-absorbing performance, the thermoplastic resin (a) is preferably a polyester compound having a tetralin ring as a structural unit, more preferably a polyester compound (a) comprising at least one structural unit having a tetralin ring selected from the group consisting of the following general formulas (1) to (4). Note that, hereinafter, the polyester compound comprising a structural unit having a tetralin ring may be referred to as a tetralin ring-containing polyester compound.

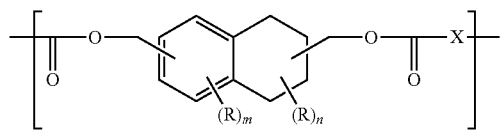
(1)

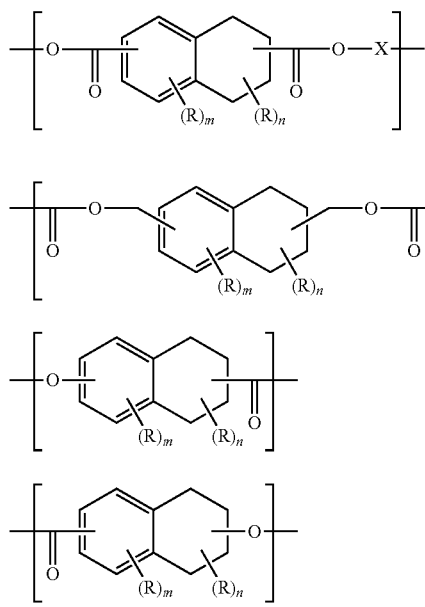
(2)

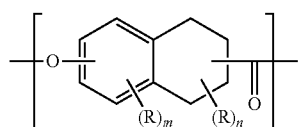
(3)

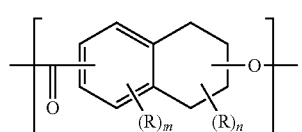
(4)

In the formulas, R independently represents a hydrogen atom or a monovalent substituent; the monovalent substituent is at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, wherein the monovalent substituent may further have a substituent; m represents an integer of 0 to 3; n represents an integer of 0 to 7; at least one hydrogen atom is bonded to the benzylic position of the tetralin ring; and X represents a divalent group comprising at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

Particularly, the structural unit represented by general formula (1) is preferably at least one selected from the group consisting of the following formulas (5) to (7). Here, "comprising a structural unit" or "having as a structural unit" means that a compound has one or more of the structural unit. Such a structural unit is preferably contained as a repeating unit in a tetralin ring-containing polyester compound. When the tetralin ring-containing polyester compound is a polymer, the polymer may be any of a homopolymer of the structural unit, a random copolymer of the structural unit and other structural units, and a block copolymer of the structural unit and other structural units.

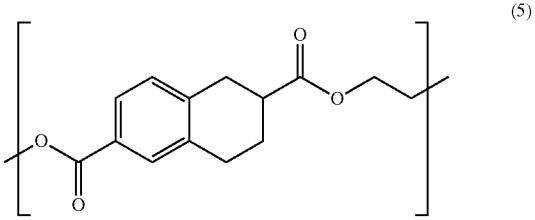
(5)

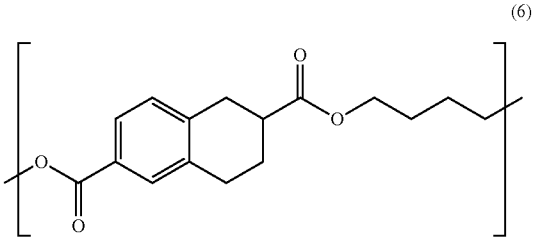
(6)

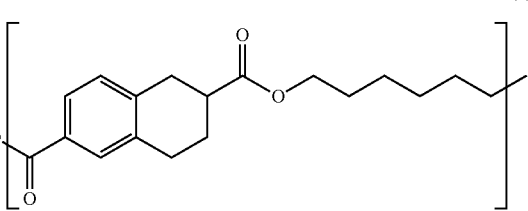
(7)

In the structural unit represented by general formulas (1) to (4), examples of the monovalent substituent represented by R include, but are not limited to, a halogen atom (such as a chlorine atom, a bromine atom, and an iodine atom), an alkyl group (a linear, branched, or cyclic alkyl group preferably having 1 to 15 carbon atoms, more preferably 1 to 6 carbon atoms; such as a methyl group, an ethyl group, a n-propyl group, an isopropyl group, a tert-butyl group, a n-octyl group, a 2-ethylhexyl group, a cyclopropyl group, and a cyclopentyl group), an alkenyl group (a linear, branched, or cyclic alkenyl group preferably having 2 to 10 carbon atoms, more preferably 2 to 6 carbon atoms; such as a vinyl group and an allyl group), an alkynyl group (an alkynyl group preferably having 2 to 10 carbon atoms, more preferably 2 to 6 carbon atoms; such as an ethynyl group and a propargyl group), an aryl group (an aryl group preferably having 6 to 16 carbon atoms, more preferably 6 to 10 carbon atoms; such as a phenyl group and a naphthyl group), a heterocyclic group (a monovalent group obtained by removing one hydrogen atom from a 5-membered or 6-membered, aromatic or non-aromatic heterocyclic compound, preferably having 1 to 12 carbon atoms, more preferably 2 to 6 carbon atoms; such as a 1-pyrazolyl group, a 1-imidazolyl group, and a 2-furyl group), a cyano group, a hydroxy group, a carboxyl group, an ester group, an amide group, a nitro group, an alkoxy group (a linear, branched, or cyclic alkoxy group preferably having 1 to 10 carbon atoms, more preferably 1 to 6 carbon atoms; such as a methoxy group and an ethoxy group), an aryloxy group (an aryloxy group preferably having 6 to 12 carbon atoms, more preferably 6 to 8 carbon atoms; such as a phenoxy group), an acyl group (a formyl group is included. An alkylcarbonyl group preferably having 2 to 10 carbon atoms, more preferably 2 to 6 carbon atoms and an arylcarbonyl group preferably having 7 to 12 carbon atoms, more preferably 7 to 9 carbon atoms; such as an acetyl group, a pivaloyl group, and a benzoyl group), an amino group (an alkylamino group preferably having 1 to 10 carbon atoms, more preferably 1 to 6 carbon atoms, an anilino group preferably having 6 to 12 carbon atoms, more preferably 6 to 8 carbon atoms, and a heterocyclic amino group preferably having 1 to 12 carbon atoms, more preferably 2 to 6 carbon atoms; such as an amino group, a methylamino group, an anilino group), a thiol group, an alkylthio group (an alkylthio group preferably having 1 to 10 carbon atoms, more preferably 1 to 6 carbon atoms; such as a methylthio group and an ethylthio group), an arylthio group (an arylthio group preferably having 6 to 12 carbon atoms, more preferably 6 to 8 carbon atoms; such as a phenylthio group), a heterocyclic thio group (a heterocyclic thio group preferably having 2 to 10 carbon atoms, more preferably 1 to 6 carbon atoms; such as a 2-benzothiazolylthio group), and an imide group (an imide group preferably having 2 to 10 carbon atoms, more preferably 4 to 8 carbon atoms; such as an N-succinimide group and an N-phthalimide group).

Note that when the above monovalent substituent R has a hydrogen atom, the hydrogen atom may be further replaced by a substituent T (here, the substituent T has the same meaning as that described in the above monovalent substituent R). Specific examples thereof include, but are not limited to, an alkyl group substituted with a hydroxy group (such as a hydroxyethyl group), an alkyl group substituted with an alkoxy group (such as a methoxyethyl group), an alkyl group substituted with an aryl group (such as a benzyl group), an alkyl group substituted with a primary amino group or a secondary amino group (such as an aminoethyl group), an aryl group substituted with an alkyl group (such as a p-tolyl group), and an aryloxy group substituted with an alkyl group (such as a 2-methylphenoxy group).

Note that when the above monovalent substituent R has a monovalent substituent T, the above number of carbon atoms of the substituent T are not included in the number of carbon atoms described above. For example, a benzyl group is regarded as an alkyl group having one carbon atom substituted with a phenyl group, and is not regarded as an alkyl group having seven carbon atoms substituted with a phenyl group. Further, when the above monovalent substituent R has a substituent T, a plurality of the substituents T may be present.

In the structural unit represented by general formulas (1) to (4), X represents a divalent group comprising at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group. The aromatic hydrocarbon group, the saturated or unsaturated alicyclic hydrocarbon group, the linear or branched, saturated or unsaturated aliphatic hydrocarbon group, and the heterocyclic group may be substituted or unsubstituted. X may contain a hetero atom, and may contain an ether group, a sulfide group, a carbonyl group, a hydroxy group, an amino group, a sulfoxide group, a sulfone group, and the like. Examples of the aromatic hydrocarbon group include, but are not limited to, an o-phenylene group, a m-phenylene group, a p-phenylene group, a methylphenylene group, an o-xylylene group, a m-xylylene group, a p-xylylene group, a naphthylene group, an anthracenylene group, a phenanthrylene group, a biphenylene group, and a fluorenylene group. Examples of the alicyclic hydrocarbon group include, but are not particularly limited to, cycloalkylene groups such as a cyclopentylene group, a cyclohexylene group, a methylcyclohexylene group, a cycloheptylene group, and a cyclooctylene group, and cycloalkenylene groups such as a cyclohexenylene group. Examples of the aliphatic hydrocarbon group include, but are not limited to, linear or branched alkylene groups such as a methylene group, an ethylene group, a trimethylene group, a propylene group, an isopropylidene group, a tetramethylene group, an isobutylene group, a tert-butylene group, a pentamethylene group, a hexamethylene group, a heptamethylene group, an octamethylene group, a nonamethylene group, and a decamethylene group, and alkenylene groups such as a vinylene group, a propenylene group, a 1-butenylene group, a 2-butenylene group, a 1,3-butadienylene group, a 1-pentenylene group, a 2-pentenylene group, a 1-hexenylene group, a 2-hexenylene group, and a 3-hexenylene group. These may further have a substituent, and specific examples thereof include, but are not limited to, a halogen atom, an alkoxy group, a hydroxy group, a carboxyl group, a carboalkoxy group, an acyl group, a thio group (such as an alkylthio group, a phenylthio group, a tolylthio group, and a pyridylthio group), an amino group (such as an unsubstituted amino group, a methylamino group, a dimethylamino group, and a phenylamino group), a cyano group, and a nitro group.

The polyester compound (a) comprising the structural unit represented by general formula (1) can be produced, for example, by a known method. For example, it can be produced by polymerizing a tetralin dicarboxylic acid alkyl ester corresponding to a monomer.

A structural unit which does not have a tetralin ring may also be incorporated into the polyester compound (a) of the present embodiment as a copolymerization component as long as that does not adversely affect performance. Specifically, compounds such as aliphatic dicarboxylic acids such as adipic acid and sebacic acid, benzene dicarboxylic acids such as terephthalic acid, and naphthalene dicarboxylic acids such as 2,6-naphthalene dicarboxylic acid can be used as other copolymerization components.

Preferred specific examples of the polyester compound (a) comprising the structural unit represented by general formula (1) include, but are not limited to, those comprising the structural units represented by the above formulas (5) to (7) and the following formulas (8) to (10). Among these, polyester compounds comprising the structural unit represented by any of the formulas (5) to (7) are preferred.

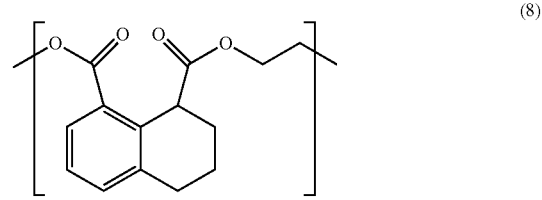

(8)

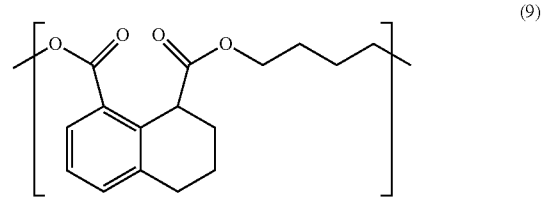

(9)

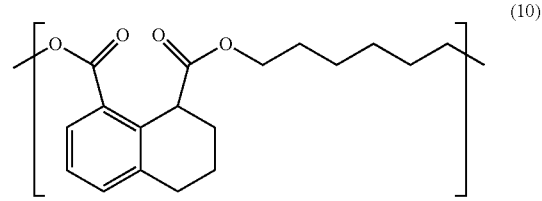

(10)

All of the above polyester compounds (a) have hydrogen at the benzylic position of the tetralin ring. When the polyester compound (a) is used in combination with a transition metal catalyst, hydrogen at the benzylic position is drawn, thereby developing excellent oxygen-absorbing power (however, the action of the present embodiment is not limited to these).

Further, the oxygen-absorbing resin composition as above can also suppress the production of a low molecular weight compound after oxygen absorption. The reason is not clear, but, for example, the following oxidation reaction mechanism can be estimated. That is, it is believed that, in the polyester compound (a), hydrogen at the benzylic position of the tetralin ring is first drawn to produce a radical, and that then a carbon at the benzylic position is oxidized by the reaction of the radical with oxygen to produce a hydroxy group or a ketone group. Therefore, the followings are estimated: since the molecular chains are not cut by oxidation reaction to thereby maintain the structure of the polyester compound (a) in the oxygen-absorbing resin composition of the present embodiment, a low molecular weight organic compound causing an odor is hardly produced after oxygen absorption; as a result, an increase in odor intensity after oxygen absorption is suppressed; and additionally, incorporation of the low molecular weight compound into the contents is prevented (however, the action of the present embodiment is not limited to these).

The intrinsic viscosity of the polyester compound (a) of the present embodiment (a measured value at 25° C. obtained by using a mixed solvent of phenol and 1,1,2,2-tetrachloroethane in a mass ratio of 6:4 (phenol:1,1,2,2-tetrachloroethane)) is, but not limited to, preferably 0.1 to 2.0 dL/g, more preferably 0.5 to 1.5 dL/g, from the point of view of the moldability of the polyester compound (a).

The glass transition temperature of the thermoplastic resin (a) ($Tg^1$) is not particularly limited, and is preferably 60 to 80° C., more preferably 62 to 78° C., and further preferably 65 to 75° C.

The content of the thermoplastic resin (a) in the layer A is not particularly limited, and is preferably 50 to 100% by mass, more preferably 70 to 100% by mass, and further preferably 90 to 100% by mass. The oxygen-absorbing power can be further improved by adjusting the content of the thermoplastic resin (a) to the above range.

(Transition Metal Catalyst)

The transition metal catalyst used in the oxygen-absorbing resin composition of the present embodiment can be arbitrarily selected from known transition metal catalysts and is not particularly limited as long as it can act as a catalyst of the oxidation reaction of the thermoplastic resin (a) having a tetralin ring as a structural unit.

Specific examples of the transition metal catalyst include an organic acid salt, a halide, a phosphate, a phosphite, a hypophosphite, a nitrate, a sulfate, an oxide, a hydroxide, and the like of a transition metal. Here, examples of a transition metal contained in the transition metal catalyst include, but are not limited to, titanium, vanadium, chromium, manganese, iron, cobalt, nickel, copper, zinc, ruthenium, and rhodium. Among these, manganese, iron, cobalt, nickel, and copper are preferred. Further, examples of an organic acid include, but are not limited to, acetic acid, propionic acid, octanoic acid, lauric acid, stearic acid, acetylacetone, dimethyldithiocarbamic acid, palmitic acid, 2-ethyl hexanoic acid, neodecanoic acid, linoleic acid, tall oil acid, oleic acid, capric acid, and naphthenic acid. The transition metal catalyst is preferably obtained by combining these transition metals with organic acids, and more preferred are combinations of manganese, iron, cobalt, nickel, or copper as a transition metal with acetic acid, stearic acid, 2-ethyl hexanoic acid, oleic acid, or naphthenic acid as an organic acid. Note that the transition metal catalyst may be used singly or in combination of two or more.

The amount of the transition metal catalyst to be blended can be arbitrarily set depending on, but not limited to, the type and desired performance of the thermoplastic resin (a) and transition metal catalyst to be used. From the point of view of the amount of oxygen absorbed in the oxygen-absorbing layer, the amount of the transition metal catalyst to be blended is preferably 0.0001 to 10 parts by mass, more preferably 0.0002 to 2 parts by mass, further preferably 0.0005 to 1 part by mass, in terms of the amount of a transition metal, based on 100 parts by mass of the thermoplastic resin (a).

The thermoplastic resin (a) and the transition metal catalyst can be mixed by a known method, but are preferably kneaded with an extruder. Thereby, an oxygen-absorbing resin composition having good dispersibility can be obtained. Further, other additives, such as a drying agent, a pigment, a dye, an antioxidant, a slipping agent, an antistatic agent, a stabilizer; a filler such as calcium carbonate, clay, mica, and silica; and a deodorant, may be added to the oxygen-absorbing resin composition as long as that does not impair the effects of the present embodiment. However, other additives are not limited to those described above, but various materials may be used in combination.

Note that the oxygen-absorbing layer may further contain a radical generator and a photoinitiator as needed in order to accelerate the oxygen absorption reaction. Further, the oxygen-absorbing resin composition may also be kneaded with thermoplastic resins other than the thermoplastic resin (a) in an extruder as long as that does not obstruct an object of the present embodiment. Known materials may be used as these radical generators, photoinitiators, and other thermoplastic resins. Examples of radical generators include N-hydroxy imide compounds such as N-hydroxy succinimide and N-hydroxy maleimide. Examples of photoinitiators include benzophenone and a derivative thereof, a thiazine dye, a metalloporphyrin derivative, an anthraquinone derivative. Examples of other thermoplastic resins include polyolefin typified by polyethylene, an ethylene-vinyl compound copolymer, a styrenic resin, a polyvinyl compound, polyamide, polyester, and polycarbonate.

The thickness of the oxygen-absorbing layer (layer A) is, but not limited to, preferably 1 to 1000 μm, more preferably 2 to 800 μm, further preferably 5 to 700 μm. The oxygen-absorbing properties of the layer A can be further increased, and the economical efficiency can be prevented from being impaired, by controlling the thickness of the layer A in the above range.

[Layer (Layer B) Comprising Thermoplastic Resin (b)]

The layer B in the present embodiment is a layer comprising a thermoplastic resin (b). Note that the layer B is generically referred to as "layer B" including the layer B1 and the layer B2, unless otherwise specified. Likewise, when thermoplastic resins (b1), (b2) are described, the "thermoplastic resin (b)" is generically referred to as a thermoplastic resin (b) including those. The thermoplastic resin (b) is a thermoplastic resin other than the thermoplastic resin (a). The content of the thermoplastic resin (b) in the layer B is, but not limited to, preferably 70 to 100% by mass, more preferably 80 to 100% by mass, further preferably 90 to 100% by mass. Note that, in the case of an embodiment in which there are a plurality of layers comprising the thermoplastic resin (b), such as the layers B1 and B2, the content of the thermoplastic resin (b) in the layer B as described here refers to the content of a thermoplastic resin (b) in each layer.

The oxygen-absorbing multilayer body of the present embodiment may have a plurality of layers B as above, such as the layers B1 and B2 as described above. When the container has a plurality of layers B, the structure of the layer B may be the same or different from each other. The thickness of the layer B may be arbitrarily determined depending on applications. Generally, when the oxygen-absorbing multilayer body is used for a multilayer container, the thickness of the layer B is preferably 5 μm to 1,000 μm, more preferably 10 μm to 800 μm, further preferably 20 μm to 500 μm from the point of view of securing various physical properties such as flexibility and strength such as falling resistance required for the multilayer container.

Any thermoplastic resins other than the thermoplastic resin (a) can be used as the thermoplastic resin (b) without limitation. Specific examples of the thermoplastic resin (b) include known resins such as polyolefin, polyester, polyamide, an ethylene-vinyl alcohol copolymer, a plant-derived resin, and a chlorine-based resin. The thermoplastic resin (b) preferably includes at least one selected from the group consisting of these resins. Among these, polyolefin is preferred. More specific suitable examples include a copolymer in which norbornene and an olefin such as ethylene are used as raw materials; and a cycloolefin copolymer (COC) which is a copolymer in which tetracyclododecene and an olefin such as ethylene are used as raw materials. Further, a cycloolefin polymer (COP) is also particularly preferred, which is a polymerized product obtained by ring opening polymerization of norbornene followed by hydrogenation. Those described, for example, in Japanese Patent Laid-Open No. 5-300939 and Japanese Patent Laid-Open No. 5-317411 can also be used as these COC and COP.

A commercially available product can be used as the COC. For example, APEL (registered trade name) manufactured by Mitsui Chemicals, Inc. is commercially available. A commercially available product can be used as the COP. For example, it is commercially available as ZEONEX (registered trade name). The COC and the COP are particularly preferred materials because chemical properties such as heat resistance and light resistance, and chemical resistance show the feature of a polyolefin resin, and physical properties such as mechanical properties, melting and flow characteristics, and dimensional accuracy show the feature of an amorphous resin.

The glass transition temperature of the thermoplastic resin (b) ($Tg^2$) is preferably 60 to 80° C., more preferably 62 to 78° C., and further preferably 65 to 75° C. When the glass transition temperature of the thermoplastic resin (b) ($Tg^2$) is in the above temperature range, molded products having good appearance can be prepared by multilayer molding with the thermoplastic resin (a).

(Layer Structure of Oxygen-Absorbing Multilayer Body and Other Matters)

The oxygen-absorbing multilayer body may further comprise arbitrary layers depending on desired performance and the like, in addition to the oxygen-absorbing layer (layer A) and the layer comprising the thermoplastic resin (b) (layer B). Examples of such an arbitrary layer include an adhesive layer (layer AD). For example, in a structure in which the layer B is formed on the layer A, the structure may be a structure in which the layer B is formed on the layer A through the layer AD (layer A/layer AD/layer B).

In an oxygen-absorbing multilayer body, when practical interlaminar bonding strength is not obtained between two adjacent layers, it is preferred to provide an adhesive layer (layer AD) between these two layers. The adhesive layer preferably comprises a thermoplastic resin having adhesive properties. Examples of the thermoplastic resin having adhesive properties include acid-modified polyolefin resins in which a polyolefin-based resin such as polyethylene or polypropylene is modified with an unsaturated carboxylic acid such as acrylic acid, methacrylic acid, maleic acid, maleic anhydride, fumaric acid, or itaconic acid; and polyester-based thermoplastic elastomers having a polyester-based block copolymer as the main component. In the adhesive layer, it is preferred to use a resin obtained by modifying a resin of the same type as the thermoplastic resin used for the layer B from the point of view of adhesive properties. From the point of view of securing molding processability while exhibiting practical adhesive strength, the thickness of the adhesive layer is preferably 2 to 100 μm, more preferably 5 to 90 μm, further preferably 10 to 80 μm.

The production method of the sterilized oxygen-absorbing multilayer body in the present embodiment is not particularly limited, but can be produced by a common injection molding process.

For example, a material forming the layer A and a material forming the layer B can be injected into a cavity from each injection cylinder through a mold hot runner using a molding machine equipped with two or more injection machines and an injection mold to produce a multilayer container corresponding to the shape of the injection mold.

Further, a material forming the layer B is first injected from an injection cylinder; a material forming the layer A is then injected from a separate injection cylinder simultaneously with the resin forming the layer B; and then a required amount of the resin forming the layer B is injected to fill a cavity, thus capable of producing a multilayer container having a three-layered structure of B/A/B.

Further, a material forming the layer B is first injected; a material forming the layer A is individually injected; and a required amount of the material forming the layer B is finally injected to fill a mold cavity, thus capable of producing a multilayer container having a five-layered structure of B/A/B/A/B.

Further, a material forming the layer B1 is first injected from an injection cylinder; a material forming the layer B2 is then injected from a separate injection cylinder simultaneously with the resin constituting the layer B1; a resin forming the layer A is then injected simultaneously with the resins forming the layer B1 and the layer B2; and a required amount of the resin forming the layer B1 is then injected to fill a cavity, thus capable of producing a multilayer container having a five-layered structure of B1/B2/A/B2/B1.

Further, a multilayered molded product may be obtained by a compression molding process. For example, a molded product can be obtained by providing an oxygen-absorbing resin agent in a thermoplastic resin molten material, feeding the molten lump to a male mold, compressing the molten lump with a female mold, and cooling and solidifying the compression molded material.

In order to give heat resistance to a top neck part of the molded product obtained, the top neck part may be crystallized by heat treatment at this stage. The degree of crystallinity is preferably 30 to 50%, more preferably 35 to 45%. Note that the crystallization may be performed after the secondary fabrication to be described below is performed.

Further, materials may be formed into a desired container shape by molding means such as extrusion molding and compression molding (sheet molding, blow molding).

The form of the oxygen-absorbing multilayer body used in the present embodiment is not particularly limited, and may be a film or an oxygen-absorbing multilayer container. Examples of the shape of the oxygen-absorbing multilayer container of the present embodiment include, but are not limited to, a bag, a tray, a cup, a bottle, a tube, PTP (a press through pack, also referred to as a blister), a vial, an ampoule, a prefilled syringe, and a vacuum blood collecting tube.

[Sterilizing Step]

The sterilizing step in the present embodiment is a step of irradiating with radiation an oxygen-absorbing multilayer body comprising at least an oxygen-absorbing layer containing a transition metal catalyst and a thermoplastic resin (a) having a tetralin ring as a structural unit (layer A) and a layer containing a thermoplastic resin (b) (layer B). According to the production method of the present embodiment, by subjecting the oxygen-absorbing multilayer body to a sterilization treatment with radiation in the sterilizing step (hereinafter may be simply referred to as "sterilization treatment with radiation"), the oxygen-absorbing multilayer body may be used, for example, as a container for food, beverages, drugs, cosmetics and the like.

(Sterilization Treatment with Radiation)

The sterilization treatment with radiation of the present embodiment is performed by irradiating with at least one selected from gamma rays and X-rays classified as electromagnetic waves; and electron beams classified as particle beams. The gamma rays that can be used in the gamma irradiation generally include, but are not limited to, gamma rays emitted from a $Co^{60}$ radiation source which is a radioisotope of Co. Further, X-rays that can be used in the X-ray irradiation generally include, but are not limited to, X-rays generated by applying electron beams accelerated in a X-ray tube or a Crookes tube using Cu, Mo, W, or the like as an anticathode. Further, electron beams that can be used in the electron beam irradiation generally include, but are not limited to, electron beams having an energy of 150 to 10000 KeV emitted from various electron beam accelerators such as a Cockcroft-Walton type, a Van der Graaff type, a resonance transformer type, an insulated core transformer type, a linear accelerator, an electrostatic accelerator, a Dynamitron type, and a high frequency cyclotron.

In the radiation sterilization treatment of the present embodiment, the dose of the radiation to be irradiated is, but not limited to, preferably 1 kGy to 200 kGy, more preferably 10 kGy to 150 kGy, further preferably 20 kGy to 100 kGy, further more preferably 20 kGy to 55 kGy, from the point of view of suppressing the degradation of resin constituting the oxygen-absorbing multilayer body.

In the present embodiment, the timing of performing the sterilization treatment with radiation to the oxygen-absorbing multilayer body is not particularly limited at all, but it is preferred to perform the sterilization treatment with radiation immediately after the preparation of the multilayer body from the point of view of reducing the contamination risk before the sterilization treatment with radiation.

Since the oxygen-absorbing multilayer body is colored by the sterilization treatment with radiation, whether the sterilization treatment has been performed or not can be confirmed by checking the color before the heat treatment to be described below. That is, the coloration can be utilized as an indicator of the sterilization treatment with radiation for the oxygen-absorbing multilayer body.

[Heating Step]

The heating step in the present embodiment is a step of heating the oxygen-absorbing multilayer body which has been irradiated with radiation in the sterilizing step at a temperature of the glass transition temperature of the thermoplastic resin (a) minus 20° C. or more and lower than the glass transition temperature of the thermoplastic resin (a) for 50 hours or more. According to the production method of the present embodiment, coloration of the oxygen-absorbing multilayer body caused by the sterilization treatment with radiation can be faded by subjecting the oxygen-absorbing multilayer body to a heating treatment in the heating step. At that stage, by adopting the condition that heating in the heating step of the present embodiment is performed at a temperature of the glass transition temperature of the thermoplastic resin (a) minus 20° C. or more and lower than the glass transition temperature of the thermoplastic resin (a) for 50 hours or more, deformation and coloration due to thermal degradation of the oxygen-absorbing multilayer body caused by heating can be prevented and generation of odor in the oxygen-absorbing multilayer body caused by the sterilization treatment with radiation can be reduced while keeping oxygen-absorbing power. According to the production method of the present embodiment, odor of the oxygen-absorbing multilayer body generated in the sterilization step can be reduced while keeping oxygen-absorbing power and suppressing deformation and coloration due to thermal degradation caused by heat even when using, in particular, an oxygen-absorbing multilayer body whose moldability has been improved by reducing the difference in the glass transition temperature between the layer A and the layer B.

The heating temperature in the heating step of the present embodiment is a temperature of the glass transition temperature of the thermoplastic resin (a) minus 20° C. or more and lower than the glass transition temperature of the thermoplastic resin (a). If the upper limit of the heating temperature is higher than the glass transition temperature of the thermoplastic resin (a), the oxygen-absorbing multilayer body may be deformed or colored due to thermal degradation by heat when heated for 50 hours or more. If the lower limit of the heating temperature is less than the glass transition temperature of the thermoplastic resin (a) minus 20° C., the effect of reducing odor may not be sufficiently exhibited or the effect of fading may be reduced. The heating temperature may be determined based on the temperature of the surface of the oxygen-absorbing multilayer body at the time of heating.

The upper limit of the heating temperature is preferably not more than "the glass transition temperature of the thermoplastic resin (a) minus 5° C.," and further preferably not more than "the glass transition temperature of the thermoplastic resin (a) minus 7° C." from the point of view of sufficiently suppressing thermal deformation and coloration due to thermal degradation of the oxygen-absorbing multilayer body.

The lower limit of the heating temperature is preferably not less than "the glass transition temperature of the thermoplastic resin (a) minus 15° C.," and further preferably not less than "the glass transition temperature of the thermoplastic resin (a) minus 12° C." from the point of view of sufficiently exhibiting the effect of reducing odor of the oxygen-absorbing multilayer body and the effect of fading.

The above upper limit and the lower limit may be accordingly combined to determine the above heating conditions.

The heating time in the heating step of the present embodiment is 50 hours or more. The effect of reducing odor may not be sufficiently exhibited and the effect of fading may also be reduced when the heating time is less than 50 hours. The time when the temperature of the surface of the oxygen-absorbing multilayer body reaches the above range may be defined as the onset of the heating time.

The upper limit of the heating time is not particularly limited, and is preferably 120 hours or less, and more preferably 100 hours or less from the point of view of the above effect by heating and cost, and from the point of view of preventing thermal deformation and thermal degradation due to excessive heating. More specifically, the heating time is preferably 50 hours or more and 120 hours or less, and more preferably 70 hours or more and 100 hours or less from the point of view of the above effect and cost by heating.

The heating is performed in an atmosphere of, for example, inert gas such as nitrogen, carbon dioxide, and argon, air, vacuum, and water, but not limited thereto. It is preferable that the oxygen-absorbing multilayer body is heated in the heating step in the presence of oxygen (e.g., in air atmosphere) from the point of view of increasing the effect of reducing odor.

The device used for heat treatment are not limited at all, but known devices can be selected and used, and examples thereof include an air forced oven. Further, although heat treatment is performed after sterilization treatment with radiation, the timing is not limited at all. The heat treatment may be performed immediately after the sterilization treatment with radiation or may be performed after a specified time lapse.

The sterilized oxygen-absorbing multilayer body produced by the production method of the present embodiment is excellent in the oxygen-absorbing performance in a wide humidity conditions from low humidity to high humidity (a relative humidity of 0% to 100%) because water is not required for oxygen absorption, and are suitable for the packaging of various articles because they are excellent in the flavor maintenance of contents. Typical examples of articles to be stored include biopharmaceuticals that are susceptible to degradation in the presence of oxygen.

Biopharmaceuticals are not particularly limited as long as they contain an active ingredient derived from protein, and a wide variety of biopharmaceuticals known to those skilled in the art may be used. More specifically, biopharmaceuticals selected from the group consisting of antibody, hormone, enzyme and a complex containing those are preferred. Specific examples of biopharmaceuticals include an adrenergic antagonist, an analgesic, an anesthetic, an angiotensin blocker, an anti-inflammatory, an anxiolytic, an antiarrhythmic, an anticholinergic, an anticoagulant, an antiepileptic, an antidiarrheal, an antihistamine, an antineoplastic and an antimetabolite, an antiplastic agent, an antiulcer drug, bisphosphonate, a bronchodilator, a cardiotonic, a cardiovascular agent, a centrally acting α2 agonist, a contrast medium, a converting enzyme inhibitor, a dermatologic, a diuretic, an agent for erectile dysfunction, an abused drug, an endothelin antagonist, a hormonal drug and cytokine, a hypoglycemic, a uricosuric agent, an agent used for gout, an immunosuppressive, a lipid lowering agent, various drugs, a psychotherapeutic agent, a renin inhibitor, a serotonin antagonist, a steroid, a sympathomimetic agent, a thyroid drug and an antithyroid drug, vasodilator, a vasopeptitase inhibitor, insulin, a blood factor, a thrombolytic, hormone, a hematopoietic growth factor, interferon, an interleukin product, a vaccine, a monoclonal antibody, a tumor necrosis factor, a therapeutic enzyme, an antibody-drug conjugate, a biosimilar, erythropoietin, immunoglobulin, a somatic cell, a tissue for gene therapy and a therapeutic recombinant protein.

Other examples include, but are not limited to, various articles such as pharmaceuticals other than biopharmaceuticals, beverages, food, chemicals such as pesticides and insecticides, pet food and detergents.

The embodiment described above is for a better understanding of the present invention and should not be construed to limit the present invention. The respective elements of the embodiment, their configuration, material, requirements, shape and size are not limited to those illustrated and may be modified as needed. Elements described in different embodiments may be partly replaced with each other or combined.

EXAMPLES

Hereinafter, the present invention will be described specifically with reference to Examples and Comparative Examples, but the present invention is not limited to these. Note that NMR (nuclear magnetic resonance) measurement was performed at room temperature unless otherwise stated.

(Synthesis of Monomer)

An autoclave having an internal volume of 18 L was charged with 2.20 kg of naphthalene-2,6-dicarboxylic acid dimethyl ester, 11.0 kg of 2-propanol, and 350 g of a catalyst (containing water in an amount of 50% by weight) in which palladium is supported by activated carbon in an amount of 5%. Next, the air in the autoclave was replaced with nitrogen; the nitrogen was replaced with hydrogen; and then hydrogen was fed to the autoclave until the pressure therein reached 0.8 MPa. Then, a stirrer was started; the rotational speed thereof was adjusted to 500 rpm; the internal temperature was increased to 100° C. over 30 minutes; and hydrogen was further fed to bring the pressure to 1 MPa. Subsequently, the feeding of hydrogen was continued so as to maintain 1 MPa depending on the decrease of pressure due to the progress of reaction. Since the pressure decrease stopped after 7 hours, the autoclave was cooled, and unreacted residual hydrogen was released. Then, a reaction mixture was removed from the autoclave. The reaction mixture was filtered to remove the catalyst, and then 2-propanol was evaporated from the separated filtrate by an evaporator. To the resulting crude product was added 4.40 kg of 2-propanol, and the crude product was purified by recrystallization to obtain tetralin-2,6-dicarboxylic acid dimethyl ester at a yield of 80%. Note that NMR analysis results are as described below. $^1$H-NMR (400 MHz CDCl$_3$) δ 7.76-7.96 (2H m), 7.15 (1H d), 3.89 (3H s), 3.70 (3H s), 2.70-3.09 (5H m), 2.19-2.26 (1H m), 1.80-1.95 (1H m)

(Synthesis of Polymer)

An apparatus for producing a polyester resin equipped with a packed column type rectifier, a partial condenser, a total condenser, a cold trap, a stirrer, a heating device, and a nitrogen introducing tube was charged with 543 g of tetralin-2,6-dicarboxylic acid dimethyl ester obtained in the synthesis example of monomer, 217 g of ethylene glycol, and 0.171 g of tetrabutyl titanate obtained from the above, and heated to 230° C. in a nitrogen atmosphere to perform transesterification reaction. The reaction conversion of the dicarboxylic acid component was increased to 85% or more, and then thereto was added 0.171 g of tetrabutyl titanate. The resulting mixture was gradually heated and decompressed and subjected to polycondensation at 245° C. and 133 Pa or less to obtain a polyester compound (1).

The weight average molecular weight and the number average molecular weight of the resulting polyester compound (1) were measured by GPC (gel permeation chromatography). As a result, the weight average molecular weight in terms of polystyrene was $8.5 \times 10^4$, and the number average molecular weight was $3.0 \times 10^4$. As a result of performing measuring glass transition temperature and a melting point by DSC (Differential Scanning calorimetry), the glass transition temperature was 67° C., and the melting point were not observed since the compound was amorphous.

[Production Example of Multilayer Container (Vial)]

An injection-molded product having a three-layered structure of B/A/B was obtained under the following conditions by injecting a material forming the layer B from an injection cylinder, then injecting a material forming the layer A from a separate injection cylinder simultaneously with the resin forming the layer B, and then injecting a required amount of the resin forming the layer A to fill a cavity in an injection mold. Then, the injection-molded product was cooled to a predetermined temperature, transferred to a blow mold, and then subjected to blow molding to produce a vial (bottle part). The gross mass of the vial was set to 24 g, and the mass of the layer A was set to 30% by mass of the gross mass of the vial. A cycloolefin polymer (COP, manufactured by Zeon Corporation, trade name: ZEONEX (registered trade mark) 5000; glass transition temperature 69° C.) was used as a material forming the layer B.

(Shape of Vial)

The total length was set to 89 mm; the outer diameter was set to 40 mm ϕ; and the thickness was set to 1.8 mm. Note that an integrated injection blow molding machine (manufactured by UNILOY, model: IBS 85, providing four vials) was used for producing the vial.

(Molding Conditions for Vial)

Injection cylinder temperature for layer A: 260° C.
Injection cylinder temperature for layer B: 280° C.
Temperature of resin flow channel in injection mold: 280° C.
Blow temperature: 150° C.
Temperature of cooling water for blow mold: 15° C.

[Evaluation of Vial]

The vials obtained in Examples and Comparative Examples were measured and evaluated for the oxygen transmission rate according to the following method.

Oxygen Transmission Rate (OTR) of Vial

A molded product was measured for the oxygen transmission rate in an atmosphere of a temperature of 23° C., a relative humidity outside the molded product of 50%, and a relative humidity inside the molded product of 100%, on the 30th day from the start of the measurement. An oxygen transmission rate measurement apparatus (manufactured by MOCON, Inc., trade name: OX-TRAN 2-21 ML) was used for the measurement. It is shown that the lower the measured value, the better the oxygen barrier property. Note that the minimum limit of detection of the measurement is an oxygen transmission rate of $5 \times 10^{-5}$ ML/(0.21 atm·day·package).

Example 1

An oxygen-absorbing resin composition was obtained by dry-blending cobalt (II) stearate with 100 parts by mass of the above polyester compound (1) so that the amount of cobalt might be 0.00025 part by mass, feeding the blended material to a twin-screw extruder having two screws each having a diameter of 37 mm at a feeding rate of 30 kg/h, melt-kneading the material at a cylinder temperature of 220° C., extruding a strand from an extruder head, cooling the strand, and then pelletizing the cooled strand. An oxygen-absorbing multilayered vial was produced using the oxygen-absorbing resin composition as a material forming the layer A by the method described above. Then, the resulting oxygen-absorbing multilayered vial was irradiated in air at room temperature with 50 kGy of gamma rays emitted from a $Co^{60}$ radiation source. Next, the vial irradiated with gamma rays was put in an automatic oven (model: DS400, manufactured by Yamato Scientific Co., Ltd.) and subjected to heat treatment for 96 hours at 55° C. in air. Subsequently, the vial was cooled to room temperature and then measured for YI and the oxygen transmission rate. Furthermore, each vial after the gamma irradiation and heat treatment was put in a barrier bag made of laminated aluminum foil film together with 300 cc of air, and stored at 23° C. and 50% relative humidity (RH) for a day, and then the presence of odor in the sealed bag was checked. After the gamma irradiation and heat treatment, whether the container was deformed or not was also visually observed. The results are shown in Table 1.

Examples 2 to 6

Examples 2 to 6 were performed in the same manner as in Example 1 except that the gamma irradiation dose, heating temperature, and heating time were changed as shown in Table 1, and the oxygen-absorbing multilayered vials were measured for YI and the oxygen transmission rate, and the presence of odor and deformation was determined. The results are shown in Table 1.

Example 7

The oxygen-absorbing multilayered vial prepared in the same manner as in Example 2-1 was irradiated in air at room temperature with 50 kGy of electron beams emitted from an electron beam generator using an electrostatic accelerator. Next, the vial irradiated with electron beams was put in an automatic oven (model: DS400, manufactured by Yamato Scientific Co., Ltd.) and subjected to heat treatment for 96 hours at 55° C. in air. Subsequently, the vial was cooled to room temperature and then measured for YI and the oxygen transmission rate. Furthermore, each film after the electron beam irradiation and heat treatment was put in a barrier bag made of laminated aluminum foil film together with 300 ml of air, and stored at 23° C. and 50% relative humidity (RH) for a day, and then the presence of odor in the sealed bag was checked. After the electron beam irradiation and heat treatment, whether the container was deformed or not was also visually observed. The results are shown in Table 1.

Examples 8 to 12

Examples 8 to 12 were performed in the same manner as in Example 7 except that the electron beam irradiation dose, heating temperature, and heating time were changed as shown in Table 1, and the oxygen-absorbing multilayered vials were measured for YI and the oxygen transmission rate, and the presence of odor and deformation was determined. The results are shown in Table 1.

Examples 13 to 18

Examples 13 to 18 were performed in the same manner as in Example 1 except that the gamma irradiation dose, heating temperature, and heating time were changed as shown in Table 1, and the oxygen-absorbing multilayered vials were measured for YI and the oxygen transmission rate, and the presence of odor and deformation was determined. The results are shown in Table 1.

Comparative Example 1

Comparative Example 1 was performed in the same manner as in Example 1 except that heat treatment was not performed, and the vials were measured for YI and the oxygen transmission rate, and the presence of odor and deformation was determined. The results are shown in Table 1.

Comparative Example 2

Comparative Example 2 was performed in the same manner as in Comparative Example 1 except that the dose was set to 25 kGy, and the oxygen-absorbing multilayered vials were measured for YI and the oxygen transmission rate, and the presence of odor and deformation was determined. The results are shown in Table 1.

Comparative Example 3

Comparative Example 3 was performed in the same manner as in Example 7 except that heat treatment was not performed, and the vials were measured for YI and the oxygen transmission rate, and the presence of odor and deformation was determined. The results are shown in Table 1.

Comparative Example 4

Comparative Example 4 was performed in the same manner as in Comparative Example 3 except that the dose was set to 25 kGy, and the oxygen-absorbing multilayered vials were measured for YI and the oxygen transmission rate, and the presence of odor and deformation was determined. The results are shown in Table 1.

Comparative Example 5

Comparative Example 5 was performed in the same manner as in Example 1 except that heating time was set to 10 hours, and the vials were measured for YI and the oxygen transmission rate, and the presence of odor and deformation was determined. The results are shown in Table 1.

Comparative Example 6

Comparative Example 6 was performed in the same manner as in Example 1 except that heating temperature was set to 80° C., and the vials were measured for YI and the oxygen transmission rate, and the presence of odor and deformation was determined. The results are shown in Table 1.

Comparative Example 7

Comparative Example 7 was performed in the same manner as in Example 1 except that heating temperature was set to 45° C., and the vials were measured for YI and the oxygen transmission rate, and the presence of odor and deformation was determined. The results are shown in Table 1.

Comparative Example 8

Comparative Example 8 was performed in the same manner as in Example 1 except that heating temperature was set to 70° C., and the vials were measured for YI and the oxygen transmission rate, and the presence of odor and deformation was determined. The results are shown in Table 1.

Comparative Example 9

Comparative Example 9 was performed in the same manner as in Example 1 except that heating temperature was set to 40° C., and the vials were measured for YI and the oxygen transmission rate, and the presence of odor and deformation was determined. The results are shown in Table 1.

Comparative Example 10

Comparative Example 10 was performed in the same manner as in Example 1 except that heating time was set to 45 hours, and the vials were measured for YI and the oxygen transmission rate, and the presence of odor and deformation was determined. The results are shown in Table 1.

Comparative Example 11

Comparative Example 11 was performed in the same manner as in Example 4 except that heating time was set to 10 hours, and the vials were measured for YI and the oxygen transmission rate, and the presence of odor and deformation was determined. The results are shown in Table 1.

Comparative Example 12

Comparative Example 12 was performed in the same manner as in Example 4 except that heating temperature was set to 80° C., and the vials were measured for YI and the oxygen transmission rate, and the presence of odor and deformation was determined. The results are shown in Table 1.

Comparative Example 13

Comparative Example 13 was performed in the same manner as in Example 4 except that heating temperature was set to 45° C., and the vials were measured for YI and the oxygen transmission rate, and the presence of odor and deformation was determined. The results are shown in Table 1.

Comparative Example 14

Comparative Example 14 was performed in the same manner as in Example 4 except that heating temperature was set to 70° C., and the vials were measured for YI and the oxygen transmission rate, and the presence of odor and deformation was determined. The results are shown in Table 1.

Comparative Example 15

Comparative Example 15 was performed in the same manner as in Example 4 except that heating temperature was set to 40° C., and the vials were measured for YI and the oxygen transmission rate, and the presence of odor and deformation was determined. The results are shown in Table 1.

Comparative Example 16

Comparative Example 16 was performed in the same manner as in Example 4 except that heating time was set to 45 hours, and the vials were measured for YI and the oxygen transmission rate, and the presence of odor and deformation was determined. The results are shown in Table 1.

TABLE 1

| | Type of radiation/dose (kGy) | | Heating conditions | | YI of multilayered vial (values in the parentheses[1]) are ΔYI) | | | Oxygen transmission rate | Deformation of container | Generation of odor |
|---|---|---|---|---|---|---|---|---|---|---|
| | Gamma rays | Electron beams | Temperature/ °C. | Time/h | Before radiation irradiation | Immediately after radiation irradiation | After heat treatment | | | |
| Example 1 | 50 | — | 55 | 96 | −0.5 | 31.7 (+32.2) | 4.6 (+5.1) | Under detection limit | None | None |
| Example 2 | 50 | — | 55 | 60 | −0.3 | 31.6 (+31.9) | 5.7 (+6.0) | Under detection limit | None | None |
| Example 3 | 50 | — | 55 | 120 | −0.6 | 31.4 (+32.0) | 4.2 (+4.8) | Under detection limit | None | None |
| Example 4 | 25 | — | 55 | 96 | −0.5 | 19.6 (+20.1) | 3.8 (+4.3) | Under detection limit | None | None |
| Example 5 | 25 | — | 55 | 60 | −0.4 | 19.7 (+20.1) | 4.5 (+4.9) | Under detection limit | None | None |
| Example 6 | 25 | — | 55 | 120 | −0.5 | 19.7 (+20.2) | 3.5 (+4.0) | Under detection limit | None | None |
| Example 7 | — | 50 | 55 | 60 | −0.3 | 30.3 (+30.6) | 4.9 (+5.2) | Under detection limit | None | None |
| Example 8 | — | 50 | 55 | 96 | −0.2 | 30.5 (+30.7) | 4.4 (+4.6) | Under detection limit | None | None |
| Example 9 | — | 50 | 55 | 120 | −0.4 | 30.3 (+30.7) | 4.1 (+4.5) | Under detection limit | None | None |
| Example 10 | — | 25 | 55 | 60 | −0.6 | 17.7 (+18.3) | 4.0 (+4.6) | Under detection limit | None | None |
| Example 11 | — | 25 | 55 | 96 | −0.5 | 18.0 (+18.5) | 3.5 (+4.0) | Under detection limit | None | None |
| Example 12 | — | 25 | 55 | 120 | −0.4 | 17.7 (+18.1) | 3.3 (+3.7) | Under detection limit | None | None |
| Example 13 | 50 | — | 48 | 96 | −0.3 | 31.6 (+31.9) | 6.9 (+7.2) | Under detection limit | None | None |
| Example 14 | 25 | — | 48 | 96 | −0.5 | 19.4 (+199) | 4.6 (+4.9) | Under detection limit | None | None |
| Example 15 | 50 | — | 65 | 96 | −0.3 | 31.4 (+31.7) | 3.6 (+3.9) | Under detection limit | None | None |
| Example 16 | 25 | — | 65 | 96 | −0.3 | 19.7 (+20.0) | 3.2 (+3.5) | Under detection limit | None | None |
| Example 17 | 50 | — | 55 | 50 | −0.4 | 31.3 (+31.7) | 7.1 (+7.5) | Under detection limit | None | None |
| Example 18 | 25 | — | 55 | 50 | −0.2 | 19.3 (+19.5) | 5.9 (+6.1) | Under detection limit | None | None |
| Comparative Example 1 | 50 | — | — | — | −0.3 | 31.6 (+31.9) | — | Under detection limit | None | Generated |
| Comparative Example 2 | 25 | — | — | — | −0.3 | 19.9 (+20.3) | — | Under detection limit | None | Generated |
| Comparative Example 3 | — | 50 | — | — | −0.2 | 30.4 (+30.6) | — | Under detection limit | None | Generated |
| Comparative Example 4 | — | 25 | — | — | −0.4 | 18.1 (+18.5) | — | Under detection limit | None | Generated |
| Comparative Example 5 | 50 | — | 55 | 10 | −0.4 | 31.2 (+31.6) | 16.8 (+17.2) | Under detection limit | None | Generated |

TABLE 1-continued

| | Type of radiation/ dose (kGy) | | Heating conditions | | YI of multilayered vial (values in the parentheses[1] are ΔYI) | | | | | |
|---|---|---|---|---|---|---|---|---|---|---|
| | Gamma rays | Electron beams | Temperature/ ° C. | Time/h | Before radiation irradiation | Immediately after radiation irradiation | After heat treatment | Oxygen transmission rate | Deformation of container | Generation of odor |
| Comparative Example 6 | 50 | — | 80 | 96 | −0.3 | 31.8 (+32.1) | 3.1 (+3.4) | Under detection limit | Deformed | None |
| Comparative Example 7 | 50 | — | 45 | 96 | −0.3 | 31.3 (+31.6) | 7.7 (+8.0) | Under detection limit | None | Generated a little |
| Comparative Example 8 | 50 | — | 70 | 96 | −0.2 | 31.5 (+31.7) | 3.3 (+3.5) | Under detection limit | Slightly deformed | None |
| Comparative Example 9 | 50 | — | 40 | 96 | −0.6 | 31.9 (+32.5) | 9.4 (+10.0) | Under detection limit | None | Generated |
| Comparative Example 10 | 50 | — | 55 | 45 | −0.3 | 31.5 (+31.8) | 8.1 (+8.4) | Under detection limit | None | Generated a little |
| Comparative Example 11 | 25 | — | 55 | 10 | −0.5 | 19.4 (+19.9) | 10.1 (+10.6) | Under detection limit | None | Generated |
| Comparative Example 12 | 25 | — | 80 | 96 | −0.3 | 19.8 (+20.1) | 2.9 (+3.2) | Under detection limit | Deformed | None |
| Comparative Example 13 | 25 | — | 45 | 96 | −0.4 | 19.5 (+19.9) | 4.2 (+4.6) | Under detection limit | None | Generated a little |
| Comparative Example 14 | 25 | — | 70 | 96 | −0.5 | 19.6 (+20.1) | 3.0 (+3.5) | Under detection limit | Slightly deformed | None |
| Comparative Example 15 | 25 | — | 40 | 96 | −0.2 | 19.5 (+19.7) | 6.5 (+6.7) | Under detection limit | None | Generated a little |
| Comparative Example 16 | 25 | — | 55 | 45 | −0.3 | 19.6 (+19.9) | 6.4 (+6.7) | Under detection limit | None | Generated a little |

[1]Based on values before radiation irradiation

As shown in Table 1, the multilayered vials produced by the production method of the present embodiment in which a heating treatment was performed in appropriate conditions after the irradiation with radiation had a reduced odor and a significantly reduced YI, and their oxygen-absorbing performance was maintained even after performing the heat treatment compared with Comparative Examples. Deformation of containers and coloration due to thermal degradation were also suppressed.

This shows that the production method of the present embodiment is very effective for reducing odor caused by irradiation with radiation and suppressing deformation of containers due to heating and coloration due to thermal degradation while keeping the oxygen-absorbing performance.

The disclosure of Japanese Patent Application No. 2017-021416 filed on Feb. 8, 2017 is incorporated herein by reference in its entirety.

Furthermore, all the documents, patent applications and technical standards disclosed in the description are incorporated herein by reference to the same extent as the documents, patent applications and technical standards are specifically and individually described.

INDUSTRIAL APPLICABILITY

The sterilized oxygen-absorbing multilayer body produced by the production method of the present invention can be utilized as a material of a container for storing various objects including foods, beverages, drugs, and cosmetics, and the like.

The invention claimed is:

1. A method for producing a sterilized oxygen-absorbing multilayer body, comprising:
    irradiating with radiation an oxygen-absorbing multilayer body comprising at least an oxygen-absorbing layer containing a transition metal catalyst and a thermoplastic resin (a) having a tetralin ring as a structural unit and a layer containing a thermoplastic resin (b); and
    heating the oxygen-absorbing multilayer body which has been irradiated with radiation at a temperature of the glass transition temperature of the thermoplastic resin (a) minus 20° C. or more and lower than the glass transition temperature of the thermoplastic resin (a) for 50 hours or more.

2. The method for producing a sterilized oxygen-absorbing multilayer body according to claim 1, wherein the oxygen-absorbing multilayer body comprises at least two layers containing a thermoplastic resin (b) and the oxygen-absorbing layer is disposed between the two layers containing a thermoplastic resin (b).

3. The method for producing a sterilized oxygen-absorbing multilayer body according to claim 1, wherein the glass transition temperature of the thermoplastic resin (a) ($Tg^1$)

and the glass transition temperature of the thermoplastic resin (b) ($Tg^2$) have the relation represented by the following equation (A):

$$Tg^1 \leq Tg^2 \leq [Tg^1 + 10° \text{ C.}] \qquad \text{Equation (A).}$$

4. The method for producing a sterilized oxygen-absorbing multilayer body according to claim 1, wherein the heating time is 50 hours or more and 120 hours or less.

5. The method for producing a sterilized oxygen-absorbing multilayer body according to claim 1, wherein the heating temperature is a temperature of the glass transition temperature of the thermoplastic resin (a) minus 20° C. or more and the glass transition temperature of the thermoplastic resin (a) minus 5° C. or less.

6. The method for producing a sterilized oxygen-absorbing multilayer body according to claim 1, wherein the oxygen-absorbing multilayer body is heated in the presence of oxygen.

7. The method for producing a sterilized oxygen-absorbing multilayer body according to claim 1, wherein the thermoplastic resin (b) has a glass transition temperature of 60 to 80° C.

8. The method for producing a sterilized oxygen-absorbing multilayer body according to claim 1, wherein the oxygen-absorbing multilayer body is an oxygen-absorbing multilayer container.

9. The method for producing a sterilized oxygen-absorbing multilayer body according to claim 1, wherein
the thermoplastic resin (a) is a polyester compound comprising at least one structural unit having a tetralin ring selected from the group consisting of the following general formulas (1) to (4):

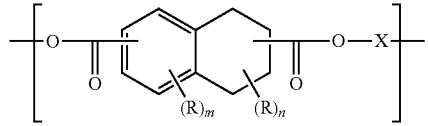
(1)

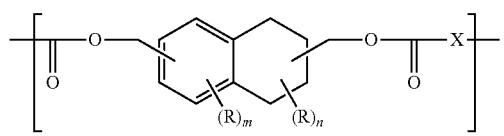
(2)

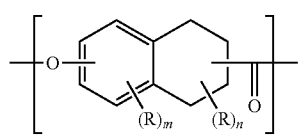
(3)

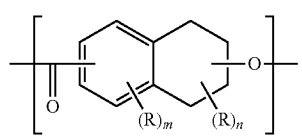
(4)

wherein R independently represents a hydrogen atom or a monovalent substituent; the monovalent substituent is at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, wherein the monovalent substituent may further have a substituent; m represents an integer of 0 to 3; n represents an integer of 0 to 7; at least one hydrogen atom is bonded to the benzylic position of the tetralin ring; and X represents a divalent group comprising at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

10. The method for producing a sterilized oxygen-absorbing multilayer body according to claim 1, wherein the transition metal catalyst contains at least one transition metal selected from the group consisting of manganese, iron, cobalt, nickel, and copper.

11. The method for producing a sterilized oxygen-absorbing multilayer body according to claim 1, wherein the transition metal catalyst is contained in an amount of 0.0001 to 10 parts by mass in terms of the amount of a transition metal based on 100 parts by mass of the thermoplastic resin (a).

12. The method for producing a sterilized oxygen-absorbing multilayer body according to claim 1, wherein the thermoplastic resin (a) is a polyester compound comprising at least one structural unit having a tetralin ring selected from the group consisting of the following general formulas (5) to (7):

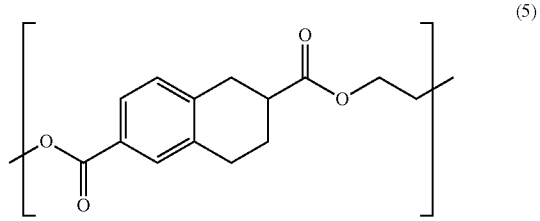
(5)

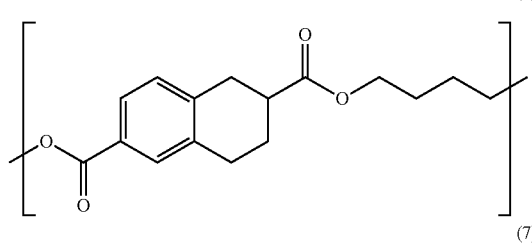
(6)

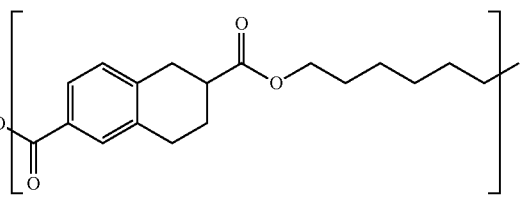
(7)

13. The method for producing a sterilized oxygen-absorbing multilayer body according to claim 1, wherein the radiation is gamma rays, X-rays, or electron beams.